United States Patent [19]
Lund et al.

[11] Patent Number: 5,529,649
[45] Date of Patent: Jun. 25, 1996

[54] INSENSITIVE HIGH PERFORMANCE EXPLOSIVE COMPOSITIONS

[75] Inventors: Gary K. Lund, Ogden; Tom K. Highsmith, North Ogden; Paul C. Braithwaite, Brigham City; Robert B. Wardle, Logan, all of Utah

[73] Assignee: Thiokol Corporation, Ogden, Utah

[21] Appl. No.: 13,034

[22] Filed: Feb. 3, 1993

[51] Int. Cl.$^6$ .................................................. C06B 45/10
[52] U.S. Cl. .................... 149/19.3; 149/19.1; 149/19.4; 149/19.5; 149/19.6; 149/19.9; 149/19.91; 149/92; 149/105; 149/19.8
[58] Field of Search .................. 149/19.1, 92, 19.3, 149/19.4, 19.5, 19.6, 19.9, 19.91, 105, 19.8

[56] References Cited

U.S. PATENT DOCUMENTS

| | | | |
|---|---|---|---|
| 3,365,454 | 1/1968 | Ferguson et al. | 260/268 |
| 3,369,020 | 2/1968 | Ferguson et al. | 260/268 |
| 4,487,938 | 12/1984 | Boileau et al. | 548/304 |
| 4,503,229 | 3/1985 | Willer | 149/92 |
| 4,747,892 | 5/1988 | Spencer | 149/92 |
| 5,034,072 | 7/1991 | Becuwe | 149/19.1 |
| 5,039,812 | 8/1991 | Norris | 149/92 |

OTHER PUBLICATIONS

Ramakrishnan et al., "4,10–Dinitro–2,6,8,12–Tetraoxa–4, 10–Diazatetracyclo[5.5.0.0$^{5,9}$0$^{3,11}$]Dodecane", *Heterocycles*, vol. 31, pp. 479–480 (1990).

*Primary Examiner*—Edward A. Miller
*Attorney, Agent, or Firm*—Ronald L. Lyons; Madson & Metcalf

[57] ABSTRACT

The use of 4,10-dinitro-2,6,8,12-tetraoxa-4,10-diazatetrocyclo[5.5.0.0$^{5,9}$0$^{3,11}$]-dodecane as the major explosive ingredient in compositions useful in high performance, low sensitivity explosive applications is disclosed.

46 Claims, No Drawings

INSENSITIVE HIGH PERFORMANCE EXPLOSIVE COMPOSITIONS

BACKGROUND OF THE INVENTION

1. Field of the Invention

This invention relates to insensitive high performance explosive compositions. More specifically, the present invention relates to the use of 4,10-dinitro-2,6,8,12-tetraoxa-4,10-diazatetracyclo[5.5.0.0$^{5,9}$0$^{3,11}$]dodecane as an explosive ingredient in compositions useful in high performance, low sensitivity explosive applications.

2. Technology Background

It is a continuing objective in the design and production of explosives to provide explosives which are highly energetic when intentionally initiated, but in which the risk of unintentional detonation is minimized. It is preferable that the mass and confinement effects of the explosive case be negligible on the probability of initiation or the transition from burning to detonation in either transport or storage. It is also preferred that if such explosive is unintentionally initiated it will be incapable of propagating to another explosive. Such explosives are termed insensitive high-explosives (IHE). Standards for IHE are discussed, for example, at pages 3–5 to 3–12 of the July 1984 DoD 6055.9-STD "Ammunition and Explosive Safety Standards" and in draft DoD-STD-2105A of Oct. 18, 1988 "Military Standard Hazard Assessment Tests For Non-Nuclear Ordnance".

Conventional IHE compositions have comprised a curable elastomeric binder in which particles of high-energy material, particularly explosive particles, oxidizers, and reactive metals, are dispersed throughout the binder. The elastomeric binder has generally been a cured elastomer, such as hydroxy-terminated polybutadienes, polypropylene glycols and the like. More recently, efforts have been made to use thermoplastic resin binders to produce insensitive high-explosives.

3-nitro-1,2,4-triazol-5-one, known in the industry as nitrotriazolone or "NTO" is a currently preferred insensitive explosive ingredient. Although explosive formulations based on NTO are less sensitive than those based on the widely used high performance explosives RDX and HMX, their poor explosive performance, compared to RDX and HMX formulations, limit the usefulness of NTO. Nitroguanidine (NQ) is another insensitive explosive ingredient commonly used in the industry, but NQ, like NTO lacks the explosive performance of conventional high performance explosives.

It would, therefore, be a substantial advancement in the art to provide a high performance explosive which was also insensitive during storage and transportation. It would be a further advancement in the art to provide an explosive ingredient useful in compositions which are high in performance, low in sensitivity and which may be used in a wide variety of explosive formulations.

Such insensitive high performance explosive compositions are disclosed and claimed herein.

SUMMARY OF THE INVENTION

The invention is directed to the use of 4,10-dinitro-2,6,8,12-tetraoxa-4,10-diazatetracyclo[5.5.0.0$^{5,9}$ 0$^{3,11}$]dodecane (herein referred to as TEX) as a major explosive ingredient in high performance, low sensitivity explosive compositions. The structure of TEX is shown below:

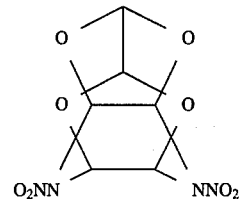

Characterization of TEX shows it to be thermally stable and significantly less impact or friction sensitive than conventional high performance solid nitramines such as RDX (1,3,5-trinitro-1,3,5-triaza-cyclohexane), HMX (1,3,5,7-tetranitro-1,3,5,7-tetraaza-cyclooctane).

TEX may be used either alone or in combination with conventional or novel solid explosive ingredients such as RDX, HMX, NTO, NQ, ADN (ammonium dinitramide), HNIW (2,4,6,8,10,12-hexanitro-2,4,6,8,10,12-hexaazatetracyclo[5.5.0.0$^{5,9}$ 0$^{3,11}$]dodecane), TATB (1,3,5-triamino-2,4,6-trinitrobenzene), DADNE (1,1-diamino-2,2-dinitro ethane), and similar compounds obvious to those skilled in the art, as the basis for formulating very high performance insensitive explosive compositions. For example, TEX may be used in combination with a binder, metal, and oxidizer to prepare low cost, castable explosives. TEX and a small amount of binder may also be used to prepare high solids (>90% TEX) pressable or extrudable explosives. Melt cast explosives may be prepared by combining TEX with an energetic or inert material having a relatively low melt temperature (<120° C.). These melt cast explosives may also contain a metal, oxidizer and other nitramine. TEX may also be used as the primary solid in simple castable formulations (up to 90% solids) using energetic or inert polymeric binders. This class of explosives may contain another nitramine (i.e., RDX, HMX), but will not normally contain an oxidizer or metal.

The explosive compositions of the present invention exhibit greatly improved explosive performance relative to current insensitive explosive compositions comprising nitrotriazolone (NTO), nitroguanidine (NQ), and various nitrate salts, all of which suffer from low performance in order to satisfy sensitivity criteria.

DETAILED DESCRIPTION OF THE INVENTION

The present invention is directed to compositions using 4,10-dinitro-2,6,8,12-tetraoxa-4,10-diazatetracyclo [5.5.0.0$^{5,9}$0$^{3,11}$]dodecane (herein referred to as TEX) as an explosive ingredient in compositions useful in high performance, low sensitivity explosive applications. The structure of TEX is shown below:

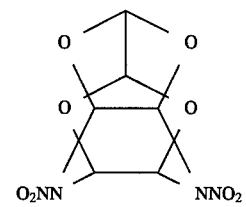

A synthesis of TEX is reported by Joseph H. Boyer and colleagues in *Heterocycles*, vol. 31, pp. 479–80 (1990), which is incorporated herein by reference. TEX may be prepared quicker and easier by reaction of diformyltetrahydroxypiperazine with nitric acid in concentrated sulfuric acid. Ammonium nitrate may also be used instead of nitric acid as a nitrate source.

The TEX as prepared often contains small measurable amounts of trioxa-trinitro-triazaisowurtzitane or tetraoxa-mononitro-monoformyl-diazaisowurtzitane and analogous isomers with progressively higher nitramine content up to and including HNIW. The inclusion of these compounds in the TEX formulations does not significantly affect the sensitivity of performance of the explosive and should be considered typical of the compositions containing TEX. Characterization of TEX shows it to be thermally stable and significantly less impact or friction sensitive than conventional high performance solid nitramines such as RDX, HMX, or HNIW. Theoretical performance calculations utilizing TEX indicate that the explosive performance of the TEX exceeds that of RDX in the neat form and is comparable to compositions containing RDX in a simple energetic binder-based plastic bonded explosive (PBX) composition.

The TEX nitramine may be used either alone or in combination with other conventional or novel solid explosive ingredients such as RDX, HMX, NTO, NQ, ADN, HNIW, TATB, DADNE, and similar compounds obvious to those skilled in the art, as the basis for formulating very high performance insensitive explosive compositions. The explosive compositions of the present invention exhibit greatly improved theoretical explosive performance relative to current insensitive explosive compositions based on NTO, NQ, and various nitrate salts, all of which suffer from low performance in order to satisfy sensitivity criteria.

The TEX nitramine may be used in the development of different types of insensitive high performance explosives. For example, TEX may be included in castable explosive formulations using a binder and optionally a metal and an oxidizer. The binder may be inert or energetic. Typical formulations may contain from about 5% to 90% TEX, preferably from about 30% to 90% TEX; from about 10% to 30% binder; from about 0% to 50% oxidizer; and from about 0% to 30% reactive metal.

When inert binders are desired, the binder is preferably hydroxy terminated polybutadiene (HTPB), although other inert binders could also be used such as PBAN (butadiene-acrylonitrile-acrylic acid terpolymer), PPG (polypropylene glycol), PEG (polyethylene glycol), polyesters, polyacrylates, polymethacrylates, CAB (cellulose acetate butyrate), and mixtures thereof. Typical energetic binders which may be used include PGN (polyglycidyl nitrate), poly-NMMO (nitratomethyl-methyloxetane), GAP (polyglycidyl azide), 9DT-NIDA (diethyleneglycol-triethyleneglycol-nitraminodiacetic acid terpolymer), poly-BAMO (poly(bisazidomethyloxetane)), poly-AMMO (poly(azidomethyl-methyloxetane)), poly-NAMMO (poly(nitraminomethyl-methyloxetane)), copoly-BAMO/NMMO, copoly-BAMO/AMMO, NC (nitrocellulose), and mixtures thereof. The binder may also contain 0% to 75% of a plasticizer such as DOA (dioctyladipate or (2-ethylhexyl)adipate), IDP (isodecylperlargonate), DOP (dioctylphthalate), DOM (dioctylmaleate), DBP (dibutylphthalate), oleyl nitrile, or mixtures thereof. Energetic plasticizers may also be used, such as BDNPF/BDNPA (bis(2,2-dinitropropyl)acetal/bis(2,2-dinitropropyl)formal), TMETN (trimethylolethanetrinitrate), TEGDN (triethyleneglycoldinitrate), DEGDN (diethyleneglycoldinitrate), NG (nitroglycerine), BTTN (butanetrioltrinitrate), alkyl NENA's (nitratoethylnitramine), or mixtures thereof.

The reactive metal is preferably aluminum or magnesium, although other reactive metals could be used such as boron, titanium, zirconium, or mixtures thereof. The oxidizer is preferably AP (ammonium perchlorate) or AN (ammonium nitrate), although other oxidizers could be used such as HAN (hydroxylammonium nitrate), ADN, or mixtures thereof. Some of the TEX may be replaced with another energetic solid such as RDX, HMX, NQ or NTO. Those skilled in the art will appreciate that the sensitivity of the final explosive formulation will depend upon its explosive ingredients; therefore, as a general rule, as the TEX concentration replacing HMX or RDX in the explosive increases, the sensitivity of the explosive decreases, while if the TEX concentration replacing NQ or NTO increases, the performance increases. This family of explosive formulations provides insensitive high performance explosives for general purpose bomb fill and underwater applications.

Another class of explosives containing TEX are the high solids, pressable or extrudable explosive formulations. The pressable or extrudable explosives have a high solids content and contain up to about 98.5% TEX, preferably from 50% to 98.5% TEX and most preferably form 80% to 98.5% TEX, or a combination of TEX and another high explosive. Various polymeric binders, including halogenated, inert and energetic binders, may be used in pressable or extrudable explosives. The polymeric binder is preferably present up to 20% by weight of the explosive composition. Although not commonly included in pressable or extrudable explosive formulations, a reactive metal and/or an oxidizer may be included in the pressable or extrudable explosive formulations of the present invention.

Halogenated polymers are preferred where high density is important. Typical halogenated polymers which may be used include Viton A® (fluorinated ethylene propylene copolymer) sold by DuPont and Kel-F® (copolymer of chlorotrifluoroethylene and vinylidene fluoride) sold by 3M. Other halogenated polymers which may be used include polyvinylidene fluoride, polydifluorochloroethylene, fluorinated polyethers, PVC (polyvinyl chloride), polytetrafluoroethylene, and mixtures thereof. Inert binders are sometimes desirable in pressable explosives because of stability and improved explosive processing. Typical inert binders which may be used include EVA (ethylenevinylacetate) and Estane® (a poly-urethane resin) sold by B. F. Goodrich. Other inert binders which may also be used include HTPB, PBAN, PPG, PEG, polyesters, polyacrylates, polymethacrylates, and CAB. Energetic binders may also be used in pressable explosives to maximize energy production and to reduce solids loading without reducing explosive performance. Typical energetic binders which may be used include PGN (polyglycidyl nitrate), poly-NMMO, GAP and NC (nitrocellulose) or CAB (cellulose acetate butyrate) plasticized with an energetic plasticizer such as a liquid nitrate ester, BDNPA, or BDNPF. BDNPA and BDNPF are sometimes blended together or made as a mixture synthetically.

Combinations of energetic solids, such as 50% TEX/40% HNIW/10% binder or 60% TEX/35% HMX/5% binder, etc. may be made to achieve the desired performance and sensitivity goals. It will be appreciated that by using TEX in this class of explosives, it is possible to achieve a wide range of performance and sensitivity goals. These explosive compositions are ideal for shaped charge or explosively formed projectile applications where a more insensitive fill is required than achievable with RDX or HMX. They are also useful for applications where more energy is required than possible with NTO or NQ, but insensitivity is still mandatory.

An additional class of explosives are those containing up to 90% TEX with the balance being a liquid polymer. These formulations may also contain a plasticizer. Both inert and energetic polymers and plasticizers may be used in this class of explosives, and another energetic solid such as HMX or RDX may replace part of the TEX to tailor the explosive properties. The polymers and plasticizers may be inert or energetic depending on the specific properties required for the particular application. The energetic binder systems may be used to maximize energy and/or to reduce solids loading while the inert binder systems may be used to increase processability and reduce sensitivity. Examples of inert polymers include HTPB, PPG, and acrylates. Typical inert plasticizers include DOA, IDP, and DOM. Typical energetic polymers useful in this class of explosives include PGN, poly-NMMO, and GAP. Energetic plasticizers include BDNPA/BDNPF, NG, DEGDN, and other nitrate esters.

Yet another class of TEX explosives are the melt cast explosives which contain TEX, or TEX in combination with another high explosive, and an energetic or inert meltable material with a relatively low melt temperature (about 120° C. or below). The meltable material acts as a "binder" to the solid explosive. Two currently preferred meltable energetic materials which may be used in the present invention are TNT (2,4,6-trinitrotoluene) and TNAZ (1,3,3-trinitroazetidine). Other meltable energetic materials which may be used include AN/NQ eutectic or alkylammonium nitrate salts. Inert meltable materials such as polyethylene and hydrocarbon wax may also be used to prepare melt cast explosive compositions within the scope of the present invention. Inert thermoplastic materials may also be used in these compositions to reduce the sensitivity. Oxidizers (AP, AN, HAN, ADN, etc.) and reactive metals (Al, Mg, B, Ti, Zr, etc.) may also be added to these melt case explosives to achieve the desired properties in a given explosive.

Typical melt cast explosive formulations within the scope of the present invention include a meltable material in the range from about 15% to 40%; TEX or blends of TEX/RDX, TEX/HMX, etc. in the range from about 5% to 85%, preferably 30% to 85%; a reactive metal from about 0% to 30%; and an oxidizer from about 0% to 30%. The reactive metal is preferably aluminum, magnesium, boron, titanium, or zirconium, although other reactive metals could be used. The oxidizer is preferably ammonium perchlorate or ammonium nitrate, although other oxidizers could be used.

For example, Composition B is a well known melt cast explosive formulation comprising 59.5% RDX, 39.5% TNT, and 1% D2 wax (84% polyethylene, 14% nitrocellulose, and 2% lecithin). A high performance, insensitive explosive may be prepared by replacing the RDX in Composition B with TEX. It will be appreciated that the percentages of TNT and TEX may be varied in such a manner that the explosive performance of Composition B is maintained or even improved.

The following examples are offered to further illustrate the present invention. These examples are intended to be purely exemplary and should not be viewed as a limitation on any claimed embodiment.

EXAMPLE 1

TEX was prepared as follows: 250 mL of concentrated sulfuric acid were placed in a 1 liter Erlenmeyer flask. The flask was placed in a water bath and stirred. To the stirred contents were added 250 mL of 90% nitric acid followed by 100 g 1,4-diformyl-2,3,5,6-tetrahydroxypiperazine at such rate that the temperature remained below 60° C. The contents were stirred for 1.5 hours over which time the temperature of the reaction dropped to ambient. The pale yellow reaction mixture was poured on to ice and the resultant precipitate collected by filtration on a glass frit. The wet solid was then returned to the flask and washed with saturated sodium bicarbonate until no more gassing was apparent. The solid was then recollected on a glass filter and washed several times with methanol to remove impurities and to facilitate drying. The product was dried in a vacuum oven overnight at 50° C. The yield was 37.62 g. The product displayed the proton and carbon NMR resonances as well as FTIR absorbances reported by Joseph H. Boyer and colleagues in *Heterocycles*, vol. 31, pp. 479–80 (1990). The chemical reaction is shown below:

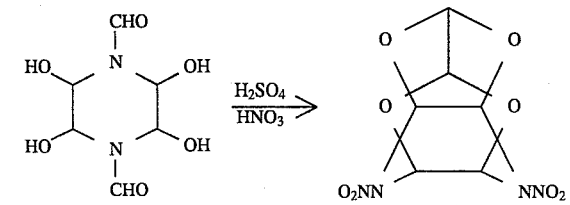

EXAMPLE 2

TEX prepared according to the procedure of Example 1 was characterized by standard chemical methods. $^1$H and $^{13}$C NMR and FTIR spectra were identical to data provided by Boyer. The material was further characterized for safety data. Safety tests were run using standard methodologies common the those skilled in the art. It should noted that TC tests are 50% values and ABL numbers are threshold initiation values. The results are as follows:

|  | Thiokol Corp. | Allegheny Ballistics Lab. |
| --- | --- | --- |
| Impact | >46 inch | 33 cm |
| Friction | >64 lb | 25 psi @ 8 ft/sec |
| Electrostatic Discharge (ESD) | 0.43 J | 0.075 J |
| Simulated Bulk Autoignition Temperature (SBAT) | onset 486° F. burned |  |

Heat of combustion ($\Delta H_c$) = 2527.5 cal/g
Heat of formation ($\Delta H_f$) = −106.5 Kcal/mol

EXAMPLE 3

Card gap testing of explosive compositions containing TEX, NTO, and RDX were conducted. In the standard "card gap" test, an explosive primer is set off a certain distance from the explosive. The space between the primer and the explosive charge is filled with an inert material such as PMMA (polymethylmethacrylate). The distance is expressed in cards, where 1 card is equal to 0.01 inch such that 70 cards is equal to 0.7 inches. If the explosive does not detonate at 70 cards, for example, then the explosive is insensitive at 70 cards.

The explosive compositions tested included 70% solids (e.g., 70% TEX, 70% NTO, and 70% RDX) in a PGN binder system comprising PGN, diethylene glycol dinitrate, and an isocyanate curative in which the plasticizer to polymer ratio was 2:1. The TEX used was prepared according to the procedure of Example 1.

The density of each explosive composition was measured and compared with its theoretical density. From this information, the theoretical detonation velocity at that density was also calculated using the standard BKW equation of state. The results are shown below:

| Energetic Solid | Measured Density g/cc | Theoretical Density g/cc | % TMD | Theoretical C.J. Velocity m/s |
| --- | --- | --- | --- | --- |
| TEX | 1.68 | 1.764 | 95.2 | 7889 |
| TEX | 1.65 | 1.764 | 93.5 | 7776 |
| NTO | 1.48 | 1.719 | 86.1 | 7039 |

-continued

| Energetic Solid | Measured Density g/cc | Theoretical Density g/cc | % TMD | Theoretical C.J. Velocity m/s |
|---|---|---|---|---|
| NTO | 1.47 | 1.719 | 85.5 | 7006 |
| RDX | 1.63 | 1.667 | 97.8 | 8042 |
| RDX | 1.61 | 1.667 | 96.6 | 7973 |

The pipes were instrumented for detonation velocity. Two tests were conducted for each explosive composition, the first test at zero cards and the second at 70 cards. The results of these tests are summarized below.

| Energetic Solid | Cards | Reaction Type | Measured Detonation Velocity (m/s) |
|---|---|---|---|
| TEX | 0 | Sustained detonation | 6811 |
| TEX | 70 | No detonation, No deflagration | |
| NTO | 0 | Sustained detonation | 6263 |
| NTO | 70 | Sustained detonation | 5571 |
| RDX | 0 | Sustained detonation | 7844 |
| RDX | 70 | Sustained detonation | 7790 |

These results support theoretical calculations that the performance of TEX is better than NTO. They also indicate reduced sensitivity for the composition based on TEX relative to both NTO and RDX.

Of the compositions tested, TEX was the least sensitive because it did not detonate at 70 cards (0.7 inches). Also pieces of the card gap pipe from the 70 cards TEX test were recovered along with pieces of unburned explosive. In the other tests, all of the explosive was consumed. In the tests with sustained detonations, a clean hole was punched through the witness plate.

EXAMPLE 4

The safety profile for TEX was compared with that of HMX and RDX and is summarized below. Safety tests were run using standard methodologies common the those skilled in the art. It should noted that TC tests are 50% values and ABL numbers are threshold initiation values.

| | Impact | | Friction | | Electrostatic Discharge | | Differential Scanning Calorimeter |
|---|---|---|---|---|---|---|---|
| | TC (inch) | ABL (cm) | TC (lb) | ABL (psi @ ft/s) | TC (J) | ABL (J) | Base Line Departure |
| HMX | 29 | 1.8 | 63 | 50/4 | 0.57 | 0.075 | ~240° C. |
| RDX | 22 | 3.5 | 63 | 130/4 | 0.43 | 0.075 | ~240° C. |
| TEX | >46 | 33 | >64 | 25/8 | 0.43 | 0.075 | ~260° C. |

With the exception of ESD, TEX appears to be quite insensitive to ignition stimuli compared to conventional nitramines.

EXAMPLE 5

Low cost HTPB binder system explosives having 85% solids were prepared according to the following formulations:

| Mix No. | Binder | Solids | | | |
|---|---|---|---|---|---|
| A* | HTPB/DOA/IPDI | Al-20% | AP-20% | NTO-25% | RDX-20% |
| B | HTPB/DOA/IPDI | Al-20% | AP-20% | TEX-25% | RDX-20% |
| C | HTPB/DOA/IPDI | Al-20% | AP-20% | TEX-45% | |
| D | HTPB/DOA/IPDI | Al-20% | AP-20% | NTO-25% | TEX-20% |

*Baseline Mix

Initial safety data is obtained for the above explosive formulations. The safety data suggests that the explosive formulations utilizing TEX provide insensitive general purpose bomb fill with performance superior to that obtained using NTO.

EXAMPLE 6

Computer modeling calculations comparing the theoretical explosive performance of several conventional explosive formulations with and without TEX were conducted utilizing the BKW equation of state. The calculations are summarized below:

| Composition | C-J Pressure (Katm) | Detonation Velocity (m/s) | Density (g/cc) |
|---|---|---|---|
| TEX/TNT 75/25 | 328.52 | 8.306 | 1.893 |
| RDX/TNT 75/25 | 324.67 | 8.435 | 1.773 |
| NTO/TNT 75/25 | 288.21 | 7.938 | 1.839 |
| NQ/TNT 75/25 | 276.86 | 8.146 | 1.695 |
| H-6† (RDX) | 232.47 | 7.300 | 1.773 |
| H-6 (TEX) | 232.77 | 7.236 | 1.852 |
| H-6 (NTO) | 216.13 | 7.057 | 1.821 |
| H-6 (NQ) | 215.16 | 7.142 | 1.735 |
| AFX-644‡ (NTO) | 242.44 | 7.312 | 1.903 |
| AFX-644 (TEX) | 260.24 | 7.487 | 1.934 |
| AFX-644 (NQ) | 239.81 | 7.384 | 1.818 |
| TEX | 370 | 8.665 | 1.990 |
| NTO | 306.99 | 8.120 | 1.910 |
| NQ | 286.39 | 8.348 | 1.710 |
| RDX | 359.58 | 8.802 | 1.820 |
| HMX | 392.56 | 9.046 | 1.900 |

†H-6 includes 74.2% Composition B, 20.6% Al, 4.7% D2 wax, and 0.5% $CaCl_2$.
‡AFX-644 includes 40% TNT, 40% NTO, 20% Al, and a trace of D2 wax.

These calculations suggest that TEX performs significantly better than NTO and NQ, about the same as RDX, and slightly lower than HMX. Given the insensitivity of compositions containing TEX, TEX and compositions based thereon, are an important additive to explosive compositions.

From the forgoing it will be appreciated that the present invention provides high performance explosives which are also insensitive during storage and transportation. The present invention further provides a new major explosive ingredient which may be used in a variety of explosive formulations for use in high performance, low sensitivity explosive applications.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A low sensitivity, high performance explosive composition comprising 4,10-dinitro-2,6,8,12-tetraoxa-4,10-diazatetracyclo[$5.5.0.0^{5,9}0^{3,11}$]-dodecane, and at least one ingredient effective to form a low sensitivity, high performance explosive.

2. A high performance explosive composition as defined in claim 1, further comprising a polymeric binder.

3. A high performance explosive composition as defined in claim 1, further comprising an oxidizer.

4. A high performance explosive composition as defined in claim 1, further comprising a reactive metal.

5. A high performance explosive composition as defined in claim 1, further comprising a meltable material.

6. A high performance explosive composition as defined in claim 1, further comprising a polymeric binder, an oxidizer, and a reactive metal.

7. A high performance explosive composition as defined in claim 5, wherein the meltable material is energetic.

8. A high performance explosive composition as defined in claim 2, wherein the polymeric binder is energetic.

9. A castable low sensitivity, high performance explosive composition comprising:
   4,10-dinitro-2,6,8,12-tetraoxa-4,10-diazatetracyclo [$5.5.0.0^{5,9}0^{3,11}$]dodecane present in the range from about 5% to about 90% by weight of the explosive composition;
   a polymeric binder present in the range from about 10% to about 30% of the explosive composition;
   an oxidizer present in the range from about 0% to 50% of the explosive composition; and
   a reactive metal present in the range from about 0% to 30% of the explosive composition.

10. A castable low sensitivity, high performance explosive composition as defined in claim 9, wherein the polymeric binder is inert.

11. A castable low sensitivity, high performance explosive composition as defined in claim 10, wherein the inert polymeric binder is HTPB (hydroxy terminated polybutadiene), PBAN (butadiene-acrylonitrile-acrylic acid terpolymer), PPG (polypropylene glycol), PEG (polyethylene glycol), polyesters, polyacrylates, polymethacrylates, CAB (cellulose acetate butyrate), or mixtures thereof.

12. A castable low sensitivity, high performance explosive composition as defined in claim 9, wherein the polymeric binder is energetic.

13. A castable low sensitivity, high performance explosive composition as defined in claim 12, wherein the energetic polymeric binder is PGN (polyglycidyl nitrate), poly-NMMO (nitratomethyl-methyloxetane), GAP (polyglycidyl azide), 9DT-NIDA (diethyleneglycol-triethyleneglycol-nitraminodiacetic acid terpolymer), poly-BAMO (poly(bisazidomethyloxetane)), poly-AMMO (poly(azidomethyl-methyloxetane)), poly-NAMMO (poly(nitraminomethyl-methyloxetane)), copoly-BAMO/NMMO, BAMO/AMMO, NC (nitrocellulose), or mixtures thereof.

14. A castable low sensitivity, high performance explosive composition as defined in claim 9, wherein the polymeric binder further comprises up to 75% of a plasticizer.

15. A castable low sensitivity, high performance explosive composition as defined in claim 14, wherein the plasticizer is inert.

16. A castable low sensitivity, high performance explosive composition as defined in claim 15, wherein the inert plasticizer is DOA (dioctyladipate), IDP (isodecylperlargonate), DOP (dioctylphthalate), DOM (dioctylmaleate), DBP (dibutylphthalate), oleyl nitrile, or mixtures thereof.

17. A castable low sensitivity, high performance explosive composition as defined in claim 14, wherein the plasticizer is energetic.

18. A castable low sensitivity, high performance explosive composition as defined in claim 17, wherein the energetic plasticizer is BDNPF/BDNPA (bis(2,2-dinitropropyl)acetal/bis(2,2-dinitropropyl)formal), TMETN (trimethylolethanetrinitrate), TEGDN (triethyleneglycoldinitrate), DEGDN (diethyleneglycol-dinitrate), NG (nitroglycerine), BTTN (butanetrioltrinitrate), alkyl NENA's (nitratoethylnitramine), or mixtures thereof.

19. A castable low sensitivity, high performance explosive composition as defined in claim 9, wherein the oxidizer is AP (ammonium perchlorate), AN (ammonium nitrate), HAN (hydroxylammonium nitrate), ADN (ammonium dinitramide), or mixtures thereof.

20. A castable low sensitivity, high performance explosive composition as defined in claim 9, wherein the reactive metal is aluminum, magnesium, boron, titanium, zirconium, or mixtures thereof.

21. A castable low sensitivity, high performance explosive composition as defined in claim 9, further comprising another explosive compound in addition to 4,10-dinitro-2, 6,8,12-tetraoxa-4,10-diazatetracyclo[5.5.0.0$^{5,9}$0$^{3,11}$]dodecane.

22. A castable low sensitivity, high performance explosive composition as defined in claim 21, wherein the other explosive compound is selected from RDX (1,3,5-trinitro-1,3,5-triaza-cyclohexane), HMX (1,3,5,7-tetranitro-1,3,5,7-tetraazacyclooctane), HNIW (2,4,6,8,10,12-hexanitro-2,4,6,8,10,12-hexaazatetracyclo[5.5.0.0$^{5,9}$0$^{3,11}$]-dodecane), ADN (ammonium dinitramide), NQ (nitroguanidine), NTO (3-nitro-1,2,4-triazol-5-one), TNAZ (1,3,3-trinitroazetidine), TATB (1,3,5-triamino-2,4,6-trinitrobenzene), DADNE (1,1-diamino-2,2-dinitro ethane), and mixtures thereof.

23. A castable low sensitivity, high performance explosive composition as defined in claim 9, wherein the 4,10-dinitro-2,6,8,12-tetraoxa-4,10-diazatetracyclo[5.5.0.0$^{5,9}$0$^{3,11}$]dodecane is present in the range from about 30% to about 90% by weight of the explosive composition.

24. A pressable or extrudable low sensitivity, high performance explosive composition comprising:

4,10-dinitro-2,6,8,12-tetraoxa-4,10-diazatetracyclo [5.5.0.0$^{5,9}$0$^{3,11}$]dodecane present up to 98.5% by weight of the explosive composition; and a polymeric binder present up to 20% by weight of the explosive composition.

25. A pressable or extrudable low sensitivity, high performance explosive composition as defined in claim 24, wherein the 4,10-dinitro-2,6,8,12-tetraoxa-4,10-diazatetracyclo[5.5.0.0$^{5,9}$0$^{3,11}$]dodecane is present in the explosive composition in the range from about 80% to about 98.5% by weight.

26. A pressable or extrudable low sensitivity, high performance explosive composition as defined in claim 24, wherein the 4,10-dinitro-2,6,8,12-tetraoxa-4,10-diazatetracyclo[5.5.0.0$^{5,9}$0$^{3,11}$]dodecane is present in the explosive composition in the range from about 50% to about 98.5% by weight.

27. A pressable or extrudable low sensitivity, high performance explosive composition as defined in claim 24, wherein the polymeric binder is halogenated.

28. A pressable or extrudable low sensitivity, high performance explosive composition as defined in claim 27, wherein the halogenated polymeric binder is fluorinated ethylene propylene copolymer, chlorotrifluoroethylene and vinylidene fluoride copolymer, polyvinylidene fluoride, polydifluorochloroethylene, fluorinated polyethers, PVC (polyvinyl chloride), polytetrafluoroethylene, or mixtures thereof.

29. A pressable or extrudable low sensitivity, high performance explosive composition as defined in claim 24, wherein the polymeric binder is inert.

30. A pressable or extrudable low sensitivity, high performance explosive composition as defined in claim 29, wherein the inert polymeric binder is EVA (ethylenevinylacetate), polyurethane, HTPB (hydroxy terminated polybutadiene), PBAN (butadiene-acrylonitrile-acrylic acid terpolymer), PPG (polypropylene glycol), PEG (polyethylene glycol), polyesters, polyacrylates, polymethacrylates, CAB (cellulose acetate butyrate), or mixtures thereof.

31. A pressable or extrudable low sensitivity, high performance explosive composition as defined in claim 24, wherein the polymeric binder is energetic.

32. A pressable or extrudable low sensitivity, high performance explosive composition as defined in claim 31, wherein the energetic polymeric binder is PGN (polyglycidyl nitrate), poly-NMMO (nitratomethyl-methyloxetane), GAP (polyglycidyl azide), 9DT-NIDA (diethyleneglycol-triethyleneglycol-nitraminodiacetic acid terpolymer), poly-BAMO (poly(bisazidomethyloxetane)), poly-AMMO (poly(azidomethyl-methyloxetane)), poly-NAMMO (poly(nitraminomethyl-methyloxetane)), copoly-BAMO/NMMO, copoly-BAMO/AMMO, NC (nitrocellulose), or mixtures thereof.

33. A pressable or extrudable low sensitivity, high performance explosive composition as defined in claim 24, wherein the 4,10-dinitro-2,6,8,12-tetraoxa-4,10-diazatetracyclo[5.5.0.0$^{5,9}$0$^{3,11}$]dodecane is combined with another explosive compound such that the 4,10-dinitro-2,6,8,12-tetraoxa-4,10diazatetracyclo[5.5.0.0$^{5,9}$0$^{3,11}$]dodecane and the other explosive compound have a combined presence in the explosive composition in the range from about 50% to about 98.5% by weight.

34. A pressable or extrudable low sensitivity, high performance explosive composition as defined in claim 33, wherein the other explosive compound is selected from RDX (1,3,5-trinitro-1,3,5-triaza-cyclohexane), HMX (1,3,5,7-tetranitro-1,3,5,7-tetraaza-cyclooctane), HNIW (2,4,6,8,10,12-hexanitro-2,4,6,8,10,12-hexaazatetracyclo[5.5.0.0$^{5,9}$0$^{3,11}$]-dodecane), ADN (ammonium dinitramide), NQ (nitroguanidine), NTO (3-nitro-1,2,4-triazol-5-one), TNAZ (1,3,3-trinitroazetidine), TATB (1,3,5-triamino-2,4,6-trinitrobenzene), DADNE (1,1-diamino-2,2-dinitro ethane), and mixtures thereof.

35. A pressable or extrudable low sensitivity, high performance explosive composition as defined in claim 24, further comprising a reactive metal.

36. A pressable or extrudable low sensitivity, high performance explosive composition as defined in claim 24, further comprising an oxidizer.

37. A melt cast low sensitivity, high performance explosive composition comprising:

4,10-dinitro-2,6,8,12-tetraoxa-4,10-diazatetracyclo [5.5.0.0$^{5,9}$0$^{3,11}$]dodecane present in the range from about 5% to about 85% by weight of the explosive composition;

an meltable material having a melting point below about 120° C. present in the range from about 15% to about 40% of the explosive composition;

an oxidizer present in the range from about 0% to 30% of the explosive composition; and a reactive metal present in the range from about 0% to 30% of the explosive composition.

38. A melt cast low sensitivity, high performance explosive composition as defined in claim 37, wherein the meltable material is energetic.

39. A melt cast low sensitivity, high performance explosive composition as defined in claim 38, wherein the energetic meltable material is TNT (2,4,6-trinitrotoluene), TNAZ (1,3,3-trinitroazetidine), AN (ammonium nitrate)/NQ (nitroguanidine) eutectic, alkylammonium nitrate salts, or mixtures thereof.

40. A melt cast low sensitivity, high performance explosive composition as defined in claim 37, wherein the meltable material is inert.

41. A melt cast low sensitivity, high performance explosive composition as defined in claim 40, wherein the inert meltable material is polyethylene, hydrocarbon wax, or mixtures thereof.

42. A melt cast low sensitivity, high performance explosive composition as defined in claim 37, wherein the oxidizer is AP (ammonium perchlorate), AN (ammonium nitrate), ADN (ammonium dinitramide), HAN (hydroxylammonium nitrate), or mixtures thereof.

43. A melt cast low sensitivity, high performance explosive composition as defined in claim 37, wherein the reactive metal is aluminum, magnesium, boron, titanium, zirconium, or mixtures thereof.

44. A melt cast low sensitivity, high performance explosive composition as defined in claim 37, wherein the 4,10-dinitro-2,6,8,12-tetraoxa-4,10-diazatetracyclo[$5.5.0.0^{5,9}0^{3,11}$]dodecane is blended with another explosive compound such that the 4,10-dinitro-2,6,8,12-tetraoxa-4,10diazatetracyclo[$5.5.0.0^{5,9}0^{3,11}$]dodecane and the other explosive compound have a combined presence in the explosive composition in the range from about 20% to about 85% by weight.

45. A melt cast low sensitivity, high performance explosive composition as defined in claim 44, wherein the other explosive compound is selected from RDX (1,3,5-trinitro-1,3,5-triaza-cyclohexane), HMX (1,3,5,7-tetranitro-1,3,5,7-tetra-azacyclooctane), HNIW (2,4,6,8,10,12-hexanitro-2,4,6,8,10,12-hexaazatetracyclo[$5.5.0.0^{5,9}0^{3,11}$]-dodecane), ADN (ammonium dinitramide), NQ (nitroguanidine), NTO (3-nitro-1,2,4-triazol-5one), TNAZ (1,3,3-trinitroazetidine), TATB (1,3,5-triamino-2,4,6-trinitrobenzene), DADNE (1,1-diamino-2,2-dinitro ethane), and mixtures thereof.

46. A melt cast low sensitivity, high performance explosive composition as defined in claim 37, wherein the 4,10-dinitro-2,6,8,12-tetraoxa-4,10-diazatetracyclo[$5.5.0.0^{5,9}0^{3,11}$]dodecane is present in the explosive composition in the range from about 30% to about 85% by weight.

\* \* \* \* \*